United States Patent [19]

Conley

[11] Patent Number: 4,658,054

[45] Date of Patent: Apr. 14, 1987

[54] PROCESS FOR THE PREPARATION OF 5,6-DIALKOXYANTHRANILIC ACIDS

[75] Inventor: Richard A. Conley, Annandale, N.J.

[73] Assignee: Ortho Pharmaceutical Corporation, Raritan, N.J.

[21] Appl. No.: 759,974

[22] Filed: Jul. 29, 1985

[51] Int. Cl.$^4$ ............................................. C07C 101/54
[52] U.S. Cl. ....................................... 562/453; 560/46; 562/423; 564/142; 564/144
[58] Field of Search ................... 560/46; 562/453, 423; 564/170, 142, 144

[56] References Cited

U.S. PATENT DOCUMENTS

| | | | |
|---|---|---|---|
| 3,238,203 | 3/1966 | Krapcho | 560/46 |
| 3,592,842 | 7/1971 | Houlihan | 562/423 |

FOREIGN PATENT DOCUMENTS

| | | | |
|---|---|---|---|
| 5542069 | 10/1980 | Japan | 562/453 |
| 694300 | 7/1953 | United Kingdom | 562/453 |

OTHER PUBLICATIONS

Meth-Cohn et al., *Chemical Abstracts*, vol. 89, No. 1973025, (1978).
Fieser et al., *Reagents for Organic Synthesis*, Wiley, New York, 1967, p. 95.
Hodges et al., *J. Am. Chem. Soc.*, vol. 86, pp. 4310–4314, 1964.

*Primary Examiner*—Natalie Trousof
*Assistant Examiner*—Bruce D. Gray
*Attorney, Agent, or Firm*—Benjamin F. Lambert

[57] ABSTRACT

A process for the preparation of 5,6-dialkoxyanthranilic acids is described. The 5,6-dialkoxyanthranilic acids are useful in the preparation of substituted quinazolinediones which are active cardiotonic agents.

10 Claims, No Drawings

PROCESS FOR THE PREPARATION OF 5,6-DIALKOXYANTHRANILIC ACIDS

The present invention relates to a method of preparing 5,6-dialkoxyanthranilic acids.

The substituted anthranilic acids which are the subject of this invention have the following formula:

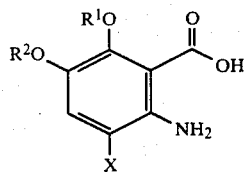

wherein X is hydrogen or halogen such as chloro or bromo and $R_1$ and $R_2$ are the same or different lower alkyl having 1-5 carbon atoms or when taken together form a methylenedioxy group.

The preparation of the substituted anthranilic acids is illustrated by the following schematic diagram:

wherein $R_1$, $R_2$ and X are as defined above, R and $R_3$ are lower alkyl having 1-4 carbon atoms and $R_4$ is n-butyl, s-butyl or t-butyl.

In each of the steps in the process, the products are isolated where indicated and characterized by techniques known to those skilled in the art.

As can be seen from the above diagram, the first step in the synthesis of a 5,6-dialkoxyanthranilic acid involves the preparation of an anilide (2) from an appropriately substituted aniline (1) such as, for example, 3,4-dimethoxyaniline, by reaction with an acid halide such as pivaloyl bromide, pivaloyl chloride or pivaloyl fluoride, or an acid anhydride such as pivalic anhydride. The reaction is carried out in a suitable solvent, such as methylene chloride or tetrahydrofuran, for example, in the presence of a base such as sodium hydroxide, potassium hydroxide or triethylamine. The reaction may be carried out at temperatures between about 5° C. and room temperature.

The anilide (2) is then reacted with an organolithium reagent such as, for example, n-butyllithium, s-butyllithium or t-butyllithium, to give the corresponding dilithium salt. The salt is then reacted in situ with carbon dioxide to give the corresponding 2'-carboxy-3',4'-

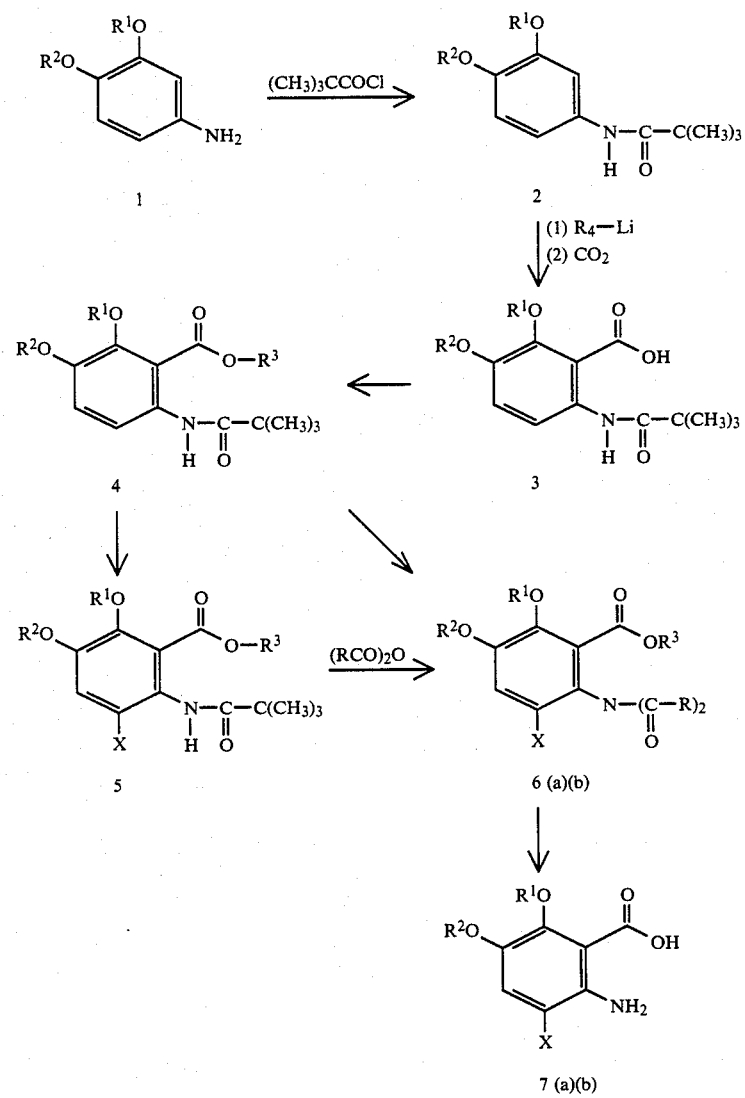

dialkoxy-2,2-dialkylpropioanilide (3). The reaction is carried out in a suitable solvent such as tetrahydrofuran or diethyl ether, for example, at a temperature ranging from about −20° C. to room temperature. The reaction is preferably carried out at 0° C. The acid (3) is then esterified with an esterifying reagent such as, for example, a dimethylformamide dialkylacetal, such as dimethylformamide dimethylacetal, a trialkylorthoformate, such as triethylorthoformate, or an alcohol and acid catalyst such as ethanol and hydrochloric acid or sulfuric acid, for example, to form the 2'-carboalkoxy-3',4'-dialkoxy-2,2-dialkylpropionanilide (4).

In the case of the halo 5,6-dialkoxy-anthranilic acid compounds, the ester (4) can be halogenated to give the corresponding haloester (5). The halogenation step is carried out in a suitable solvent such as methylene chloride, chloroform or acetic acid, for example, at a temperature between 0° C. and room temperature. The preferred reaction temperature is between about 5° C.-10° C. As the halogenating agent sulfuryl chloride, chlorine, bromine, N-bromosuccinimide and N-chlorosuccinimide may be employed. Alternatively, the acid (3) can be halogenated to give the halo acid and the halo acid is then esterified to give the haloester (5).

Either ester (4 or 5) can be converted to the N,N-diacyl-2-carboalkoxy-3,4-dialkoxy-(6-halo)-aniline (6) by reaction with an acid anhydride such as acetic anhydride, propionic anhydride and butyric anhydride, for example, in a suitable solvent such as acetic acid, propionic acid and butyric acid. The reaction is preferably carried out at the reflux temperature of the solvent.

Hydrolysis of the substituted aniline (6) with a suitable base such as sodium hydroxide or potassium hydroxide gives the substituted anthranilic acid (7).

Where not otherwise indicated in the specification, lower alkyl shall mean a hydrocarbon containing 1-4 carbon atoms and halo shall mean chloro, bromo or fluoro.

The substituted anthranilic acids are useful as intermediates in the preparation of the substituted quinazolinediones which are the subject of U.S. Ser. No. 653,620, filed Sept. 24, 1984 the subject matter of which is incorporated herein by reference. The substituted quinazolinediones are useful as cardiotonic agents.

The process of this invention eliminates the regioisomer problems associated with the preparation of the quinazolinediones disclosed in U.S. Ser. No. 653,620 while shortening the overall synthesis. Some of the intermediates prepared in the synthesis of the substituted anthranilic acids are novel compounds and as such are part of the present invention.

All of the starting materials used in the present process are either known materials or can be readily made from known materials by one skilled in the art.

The following examples describe the invention in greater particularity and are intended to be a way of illustrating but not limiting the invention.

EXAMPLE 1

3',4'-Dimethoxy-2,2-dimethylpropionanilide (2)

A solution of 368 g (2.4 mol) of 3,4-dimethoxyaniline (1) in 1400 mL of methylene chloride was prepared and treated with Darco at 25° C. for 20 minutes. After filtering through a Hyflo bed, 1320 mL of 2N sodium hydroxide was added and the reaction mixture was cooled to 10° C. Pivaloyl chloride (2.4 mol—296 mL) was added over 1 hour and the reaction mixture was then stirred for an additional hour at room temperature. The methylene chloride layer was separated, dried with magnesium sulfate, and treated with Darco*. The resultant methylene chloride solution was heated to reflux (45° C.) and 1500 mL of heptane was added. The reaction was then cooled to 30° C. and 1000 mL of 10:90 methylene chloride/heptane was added with cooling to 0° C. Filtration gave 467 g (82%) of the desired product, mp 126°–128° C. NMR (CDCl$_3$) δ 1.30 (s, 9H, C—CH$_3$), 3.83 (s, 3H, OCH$_3$), 3.87 (s, 3H, OCH$_3$), 6.80 (m, 2H, ArH), 7.27 (br s, 1H, NH), 7.42 (m, 1H, ArH).

*Activated charcoal

EXAMPLE 2

2'-Carboxy-3',4'-dimethoxy-2,2-dimethylpropioanilide (3)

A solution of 100 g (0.42 mol) of 3',4'-dimethoxy-2,2-dimethylpropioanilide (2) in 100 mL of tetrahydrofuran was prepared under a nitrogen atmosphere and cooled to 0° C. A solution of n-butyllithium in heptane (0.844 mol-538 mL-1.57M) was added and the reaction mixture was then stirred at 0° C. for 1 hour. Carbon dioxide gas was then bubbled in for 0.5 hour and the reaction mixture was then warmed to room temperature. Following dilution with 500 mL of water and acidification of pH 2 with 100 mL of concentrated hydrochloric acid, the layers were separated and the aqueous layer was extracted with 1250 mL of methylene chloride. The combined organic layers were dried over magnesium sulfate, treated with Darco, and rotary evaporated at 80° C. Heptane (500 mL) was added and the solution was cooled to crystallize the product. Filtration gave 95 g (80%) of the product as off-white crystals, mp 91°–95° C. NMR (CDCl$_3$) δ 1.33 (s, 9H, C—CH$_3$), 3.90 (s, 3H, OCH$_3$), 4.07 (s, 3H, OCH$_3$), 7.13 (d, 1H, J=10 Hz, ArH), 8.52 (d, 1H, J=10 Hz, ArH), 10.87 and 11.25 (br s, 1H, NH or CO$_2$H), 11.25 (br s, 1H, NH or CO$_2$H).

EXAMPLE 3

2'-Carbomethoxy-3',4'-dimethoxy-2,2-dimethylpropioanilide (4)

A solution of 56 g (0.2 mol) of 2'-carboxy-3',4'-dimethoxy-2,2-dimethylpropioanilide (3) in 150 mL of methylene chloride was prepared. Dimethylformamide dimethyl acetal (60 mL-0.44 mol) was added dropwise and the reaction mixture was stirred for 1.5 hr. The reaction mixture was rotary evaporated to an orange-brown oil and 150 mL of methylene chloride was added. The methylene chloride was extracted with 2×100 mL of 1N HCl, 1×100 mL of 1N NaOH, and 1×200 mL of water. The organic layer was dried over sodium sulfate, treated with Darco, and rotary evaporated to yield 50 g (85%) of a deep orange oil which solidified upon standing. Recrystallization from ethyl acetate-30°–60° C. petroleum ether gave 29 g (49%) of white product, mp 66.0°–68.5° C. NMR (CDCl$_3$) δ 1.27 (s, 9H, C—CH$_3$), 3.88 (s, 6H, OCH$_3$), 3.97 (s, 3H, OCH$_3$), 7.02 (d, 1H, J=10 Hz, ArH), 8.05 (d, 1H, J=10 Hz, ArH), 9.28 (br s, 1H, NH).

EXAMPLE 4

2'-Carbomethoxy-6'-chloro-3',4'-dimethoxy-2,2-dimethyl-propioanilide (5)

A solution of 14.8 g (50 mmol) of 2'-carbomethoxy-3',4'-dimethoxy-2,2-dimethylpropioanilide (4) in 80 mL of methylene chloride was prepared and cooled to 5° C.

Sulfuryl chloride (4.5 mL-55 mmol) was added dropwise keeping the temperature between 5°-10° C. The reaction was stirred at room temperature for 2 hours and then degassed for another hour. The reaction mixture was extracted successively with 1×50 mL of 1N NaOH, 1×25 mL of 1N NaOH, and 1×100 mL of water. The organic layer was dried over sodium sulfate, and treated with Darco. Rotary evaporation gave 15.6 g (95%) of white solid. Recrystallization from isopropanol-hexanes gave 14.5 g (88%) of the product as white crystals, mp 150.0°-151.5° C. NMR (CDCl$_3$) δ 1.43 (s, 9H, C—CH$_3$), 3.82 (s, 9H, OCH$_3$), 6.98 (s, 1H, ArH), 7.33 (br s, 1H, NH).

EXAMPLE 5

2-Carbomethoxy-N,N-diacetyl-3,4-dimethoxyaniline (6a)

A solution of 37.6 g (130 mmol) of 2'-carbomethoxy-3',4'-dimethoxy-2,2-dimethylpropioanilide (4) in 400 mL of acetic anhydride and 200 mL of acetic acid was prepared and refluxed for 22 hours. The pale yellow reaction mixture was cooled and rotary evaporated to yield 36.8 g (98%) of the product as a thick brown oil. NMR (CDCl$_3$) δ 2.25 (s, 6H,

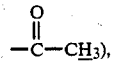

3.80 (s, 3H, OCH$_3$), 3.87 (s, 6H, O—CH$_3$), 6.83 (d, 1H, J=8 Hz, ArH), 7.03 (d, 1H, J=8 Hz, ArH).

EXAMPLE 6

2-Carbomethoxy-6-chloro-N,N-diacetyl-3,4-dimethoxyaniline (6b)

A solution of 16.5 g (50 mmol) of 2'-carbomethoxy-3',4'-dimethoxy-6'-chloro-2,2-dimethylpropioanilide (5) in 135 mL of acetic anhydride and 15 mL of glacial acetic acid was prepared and refluxed for 20 hours. The reaction mixture was rotary evaporated to 16.3 g of crude brown solid which upon recrystallization from ethyl acetate-hexanes gave the product, 14.2 g (86%), as an off-white solid, mp 100°-102° C. NMR (CDCl$_3$) δ 2.28 (s, 6H,

3.85 (s, 3H, OCH$_3$), 3.90 (s, 3H, OCH$_3$), 3.92 (s, 3H, OCH$_3$), 7.08 (s, 1H, ArH).

EXAMPLE 7

5,6-Dimethoxyanthranilic acid (7a)

A mixture of 36.8 g (130 mmol) of 2-carbomethoxy-N,N-diacetyl-3,4-dimethoxyaniline and 500 mL of 2N NaOH was prepared and heated to reflux to obtain a clear brown solution. After refluxing for 5 hours, the reaction mixture was treated with Darco and filtered through a Hyflo bed to give a clear yellow solution. Glacial acetic acid (65 mL) was added and the reaction mixture was extracted with 2×500 mL of methylene chloride. Drying over sodium sulfate and rotary evaporation gave 19.5 g (76%) of crude white product. Recrystallization from ethyl acetate-hexane gave 15.4 g (60%) of the product as a white crystalline solid, mp 92.5°-95.0° C. NMR (CDCl$_3$) δ 3.78 (s, 3H, OCH$_3$), 4.02 (s, 3H, OCH$_3$), 6.45 (d, 1H, J=10 Hz, ArH), 7.00 (d, 1H, J=10 Hz, ArH), 7.60 (br s, 3H, CO$_2$H and NH$_2$).

EXAMPLE 8

3-Chloro-5,6-dimethoxyanthranilic acid (7b)

A mixture of 2,4 g (97.3 mmol) of 2-carbomethoxy-6-chloro-N,N-diacetyl-3,4-dimethoxyaniline and 20 mL of 2N sodium hydroxide was refluxed 3.5 hours. The solution was treated with Darco and neutralized with 5 mL of glacial acetic acid. Upon cooling, the product crystallized and was collected by filtration to yield 0.6 g (36%) of a fluffy yellow solid, mp 140°-142° C. NMR (CDCl$_3$) δ 3.82 (s, 3H, OCH$_3$), 4.03 (s, 3H, OCH$_3$). 7.15 (s, 1H, ArH).

EXAMPLE 9

2'-Carboxy-6'-chloro-3',4'-dimethoxy-2,2-dimethyl-propioanilide

A solution of 7.1 g (30 mmol) of 2'-carboxy-3',4'-dimethoxy-2,2-dimethylpropioanilide in 75 mL of methylene chloride was prepared and cooled to 5° C. Sulfuryl chloride (2.9 mL/36 mmol) was added and the solution was allowed to warm to room temperature. The reaction was refluxed for 1 hour, cooled to room temperature, and extracted with 10 mL of 2N sodium hydroxide. The aqueous layer was extracted with 25 mL of methylene chloride, acidified to pH 2 with 15 mL of concentrated hydrochloric acid, and then extracted with 2×50 mL of methylene chloride. The combined methylene chloride layers were dried over magnesium sulfate and evaporated to yield 6 g (67%) of product, mp 182°-184° C.

EXAMPLE 10

2'-Carbomethoxy-6'-chloro-3',4'-dimethoxy-2,2-dimethyl-propioanilide

Treatment of 2'-carboxy-6'-chloro-3',4'-dimethoxy-2,2-dimethylpropioanilide with dimethylformamide dimethylacetal in methylene chloride as in Example 3 gives the desired product.

Preparation of a substituted quinazolinedione from a 5,6-dialkoxyanthranilic acid.

5,6-Dimethoxyquinazolin-2,4(1H,3H)-dione 5,6-Dimethoxyanthranilic acid (10.5 g, 53.2 mM) was dissolved in glacial acetic acid (100 ml) and potassium cyanate (10.8 g, 133.0 mM) in 120 ml H$_2$O was added gradually and stirred for 2 hours at 60° C. After cooling the reaction mixture to 20° C., sodium hydroxide pellets (78.2 g, 196 mole) were added while maintaining the temperature below 60° C. The reaction mixture was then heated at 90° C. for 45 minutes. Upon cooling in an ice bath, the sodium salt of the product precipitated, was filtered, resuspended in H$_2$O (120 ml), acidified (pH 3) with concentrated HCl, cooled, and filtered to give the crude product. Trituration with warm isopropanol yielded the product (60.8%) as a white solid, mp 266°-268° C.

I claim:

1. The process for the preparation of a compound of the formula which comprises reacting a compound of the formula

[structure: R¹O, R²O substituted aniline with NH₂]

with a pivalic acid compound of the formula $$X-\overset{O}{\underset{\|}{C}}-R_5$$

to form an amide of the formula

[structure: R¹O, R²O substituted aryl-NH-C(=O)-C(CH₃)₃]

reacting the amide with an organolithium compound of the formula

R₄—Li followed by reaction of the dilithium salt which forms which carbon dioxide to form an anilide of the formula

[structure: R¹O, R²O substituted benzoic acid with N(H)-C(=O)-C(CH₃)₃]

reacting the anilide with an esterifying agent to form an ester of the formula

[structure: R¹O, R²O, C(=O)O—R³, N(H)-C(=O)-C(CH₃)₃]

reacting the ester with an acid anhydride of the formula (RCO)₂O and hydrolyzing the product formed with base, wherein R, R₁, R₂, R₃ are the same or different loweralkyl, R₄ is n-butyl, s-butyl, or t-butyl, R₅ is t-butyl and X is OCOC(CH₃)₃, chloro, bromo or fluoro.

2. The process of claim 1 wherein the pivalic acid compound is pivaloyl chloride.

3. The process of claim 1 wherein the organolithium compound is n-butyllithium.

4. The process of claim 1 wherein the esterifying agent is dimethylformamide dimethylacetal.

5. The process of claim 1 wherein the acid anhydride is acetic anhydride.

6. The process of claim 1 wherein the base is sodium hydroxide.

7. The process for the preparation of a compound of the formula

[structure: R¹O, R²O, COOH, NH₂, X substituted benzene]

which comprises reacting a compound of the formula

[structure: R¹O, R²O, C(=O)O—R³, N(H)-C(=O)-C(CH₃)₃]

with a halogenating agent to form a compound of the formula

[structure: R¹O, R²O, C(=O)O—R³, N(H)-C(=O)-C(CH₃)₃, X]

reacting the product formed with an acid anhydride of the formula (RCO)₂O to form a compound of the formula

[structure: R¹O, R²O, C(=O)O—R³, N-(C(=O)-R)₂, X]

and hydrolyzing the product formed with base wherein, R, R₁, R₂ and R₃ are the same or different lower alkyl, and X is halo.

8. The process of claim 7 wherein the esterifying agent is dimethylformamide dimethylacetal.

9. The process of claim 7 wherein the acid anhydride is acetic anhydride.

10. The process of claim 7 wherein the base is sodium hydroxide.

* * * * *

UNITED STATES PATENT AND TRADEMARK OFFICE
CERTIFICATE OF CORRECTION

PATENT NO. : 4,658,054
DATED : April 14, 1987
INVENTOR(S) : Richard A. Conley

It is certified that error appears in the above—identified patent and that said Letters Patent is hereby corrected as shown below:

Column 7, Claim 1, line 40, "which carbon dioxide" should read -- with carbon dioxide --.

Signed and Sealed this

Tenth Day of November, 1987

Attest:

DONALD J. QUIGG

Attesting Officer

Commissioner of Patents and Trademarks